United States Patent [19]

Spano et al.

[11] Patent Number: 4,836,070
[45] Date of Patent: Jun. 6, 1989

[54] METHOD AND APPARATUS FOR PRODUCING FIBROUS WEB PIECES

[75] Inventors: John D. Spano, Bordentown Township, Burlington County, N.J.; Michael J. Menard, Doylestown, Pa.

[73] Assignee: Personal Products Company, Milltown, N.J.

[21] Appl. No.: 897,166

[22] Filed: Aug. 15, 1986

[51] Int. Cl.⁴ ............................................. B26D 7/18
[52] U.S. Cl. ......................................... 83/27; 83/50; 83/55; 83/81; 83/97; 83/104; 83/155; 83/257; 83/649; 83/685
[58] Field of Search .................. 83/23, 27, 40, 50, 55, 83/81, 97, 104, 155, 257, 649, 685

[56] References Cited

U.S. PATENT DOCUMENTS

| | | | |
|---|---|---|---|
| 3,116,658 | 1/1964 | Baker | 83/50 X |
| 4,085,639 | 4/1978 | Marconi | 83/685 |
| 4,500,315 | 2/1985 | Pieniak et al. | 604/379 |

Primary Examiner—Donald R. Schran

[57] ABSTRACT

A method and apparatus for producing fibrous web pieces by die cutting the pieces from a continuous web. In the method, a fibrous web is provided having adjacent corrugations usually filled with a powder, and the powder-filled web is passed through a matched cutting die set intermittently which cuts and punches out the individual web pieces. Following the web cut out step, the web pieces are transferred downwardly onto a shuttle conveyor, and the pieces moved forward and simultaneously spread apart to permit subsequent convenient placement of the pieces. The cutting die apparatus includes matched punch and body die units which closely interfit with less than about 0.001 inch total clearance, so as to cut and punch out the fibrous web pieces from the continuous web.

9 Claims, 4 Drawing Sheets

METHOD AND APPARATUS FOR PRODUCING FIBROUS WEB PIECES

This invention relates to producing fibrous web pieces and relates particularly to a method and apparatus for rapidly producing powder-filled fibrous web pieces by die cutting the pieces from a powder-filled web.

It is known to use powder-filled fibrous web pieces in absorbent structures, such as disclosed by U.S. Pat. No. 4,500,315. Such web pieces have usually been cut from continuous fibrous webs using steel rule type cutting dies. However, such dies have the disadvantage of being used against an anvil surface, after which the resulting web pieces must be picked up and transferred to another location for use. But for achieving accurate rapid positioning of web pieces, it is desirable to cut and transfer the web pieces in a single operation using punch and die type tooling. However, an important problem encountered with cutting webs containing fine fibers with conventional punch and die tooling is bending and smearing instead of cutting the fine fibers. Thus, a method and apparatus for die cutting such web pieces rapidly and clearly has not been available prior to development of the present invention.

SUMMARY OF INVENTION

This invention provides a method for producing shaped fibrous web pieces die cut from a fibrous web material, which web usually contains a powder material. The method of the invention includes providing a fibrous corrugated web, which preferably has spaces between the adjacent corrugations substantially filled with a powder material provided on the web in a powder/web weight ratio of at least about 0.5/1, then passing the web through a matched cutting die assembly, and intermittently cutting the web and punching out multiple shaped web pieces from the web. The method preferably includes providing a web having the upper side of the web filled with a powder, then passing the powder-filled web through an inverter step intermittently so as to invert the web and place the powder on the lower side of the web. The invention includes forcing the punched-out web pieces down onto a shuttle carrier containing pins located below the cutting die unit, and moving the web pieces laterally apart by the pins incorporated into the shuttle carrier. If desired, the invention also includes collecting any powder dislodged from the corrugated web on a moving belt located below the punchout die set and web pieces.

Alternatively, the undesired loss of powder from the corrugated web can be prevented by additionally covering the powder-filled side of the web with a thin fibrous facing sheet before inverting the web, so as to retain the powder in the web corrugation spaces during cutting and punching out of the web pieces. The corrugated web has a width sufficient for die cutting and punching out at least two elongated web pieces oriented in an end-to-end relationship, and preferably 4-10 web pieces are die cut intermittently and simultaneously from the powder-filled web.

The present invention also provides a cutting die apparatus for producing such fibrous web pieces. The apparatus of the invention includes means for feeding forward a fibrous web to a matched cutting die assembly and means for withdrawing a scrap strip therefrom; the cutting die assembly including a lower body unit having at least one shaped opening therein, and a vertically movable upper die body unit having at least one punch adapted to closely interfit into the lower body unit shaped openings with total clearance less than about 0.001 inch so as to die cut and punch out fibrous web pieces from the web. Shuttle conveyor means are located below said die assembly and adapted to receive the punched out web pieces, said shuttle conveyor being adapted to move the web pieces forward and laterally apart from each other simultaneously. The punch to die opening total clearance is related to the diameter of fibers in the web being cut, with the smaller die clearances being required for cutting webs having small diameter fibers. The total punch and die clearance required is less than about 0.001 inch and is preferably 0.0002-0.0008 inch.

It is an advantage of the present invention that fibrous web pieces having parallel corrugations and usually containing a powder material are rapidly die cut from a continuous web and punched out in a closely spaced relation for economic production. The pieces are conveniently deposited onto a shuttle conveyor and are subsequently moved apart laterally as required for their further handling or processing.

BRIEF DESCRIPTION OF DRAWINGS

This invention will be further described by reference to the following drawings, in which:

FIG. 3A shows a partial plan taken along view line 3A—3A of FIG. 3;

DESCRIPTION OF INVENTION

Figure 1:
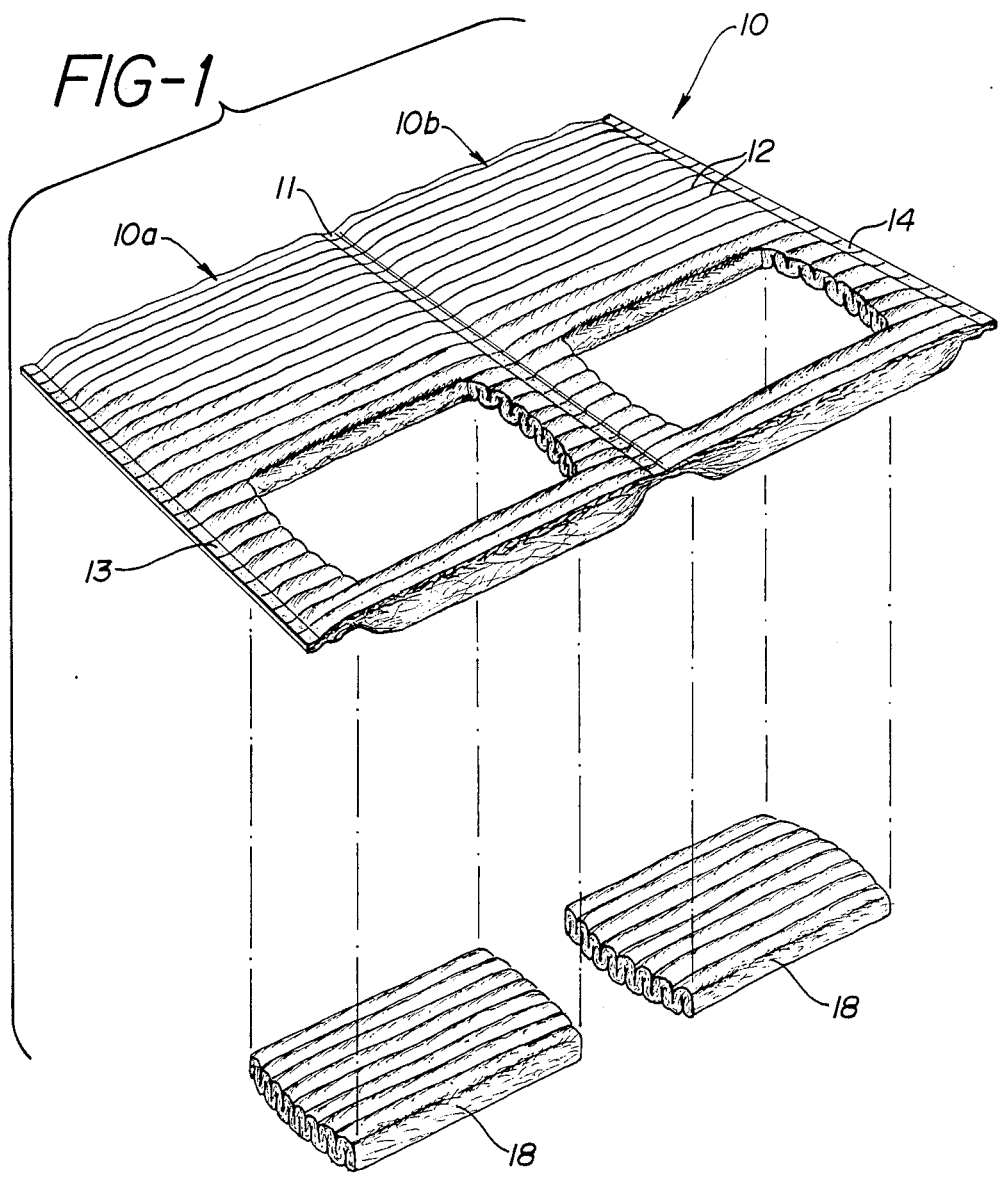
FIG. 1 shows a perspective view of a portion of a continuous fibrous web structure having transverse corrugations which may contain a powder material.

As generally shown in FIG. 1, a continuous fibrous web 10 has multiple parallel corrugations 12 provided in two parallel portions 10a and 10b of the web, which portions are separated by a central embossed band portion 11 of the web. The fibrous web 10 is also embossed at bands 13 and 14 located along each edge of the web. The web is usually formed in two layers of fibrous material, and will usually have a powder material incorporated into the lower fibrous layer. According to the present invention, fibrous web pieces 18 are die cut from the portions 10a and 10b of the web, as is further shown by FIG. 2.

Figure 2:
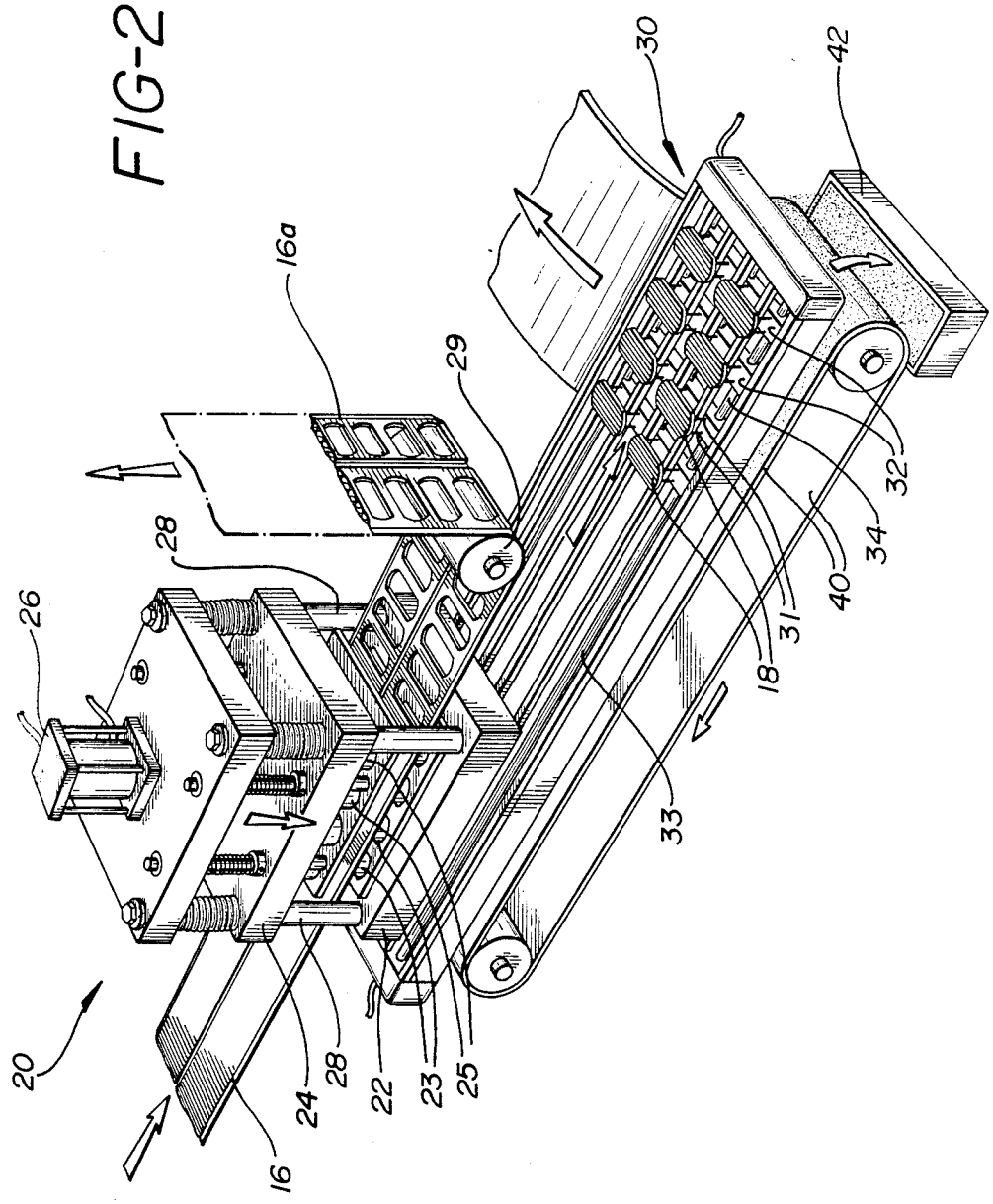
FIG. 2 shows a perspective view of a fibrous web being passed through a cutting die assembly to produce multiple web pieces, which are deposited on and moved forward by a shuttle conveyor.

As generally shown in perspective by FIG. 2, the continuous fibrous web 10 is usually fed intermittently from a prior processing step (not shown) in which a powder material is provided into the web. The resulting powder-filled web at 16 is passed to a cutting die assembly 20, which includes a lower die member 22 having at least one opening 23 and preferably having 2-10 openings 23 provided therein. Die assembly 20 also includes upper unit 24 having at least one punch 25 each closely matched dimensionally to the opening(s) 23 in the lower die member 22, so as to have a total lateral clearance between the punch lower cutting edge and the opening less than about 0.001 inch, and preferably 0.0002-0.0008 inch clearance. Intermittent vertical movement of upper die unit 24 is produced by hydraulic piston 26 and is guided by four vertical guide rods 28.

For the cutting die assembly 20, the upper and lower units are closely aligned by four vertical guide rods 28, which each have total lateral clearances less than about 0.0008 inch between the rods and their mating bushings. The upper die punch unit consists of two member, a lower member which descends first and clamps the web onto the die face, after which the punch upper member 25 descends into the openings 23 to cut out the fibrous web pieces 18 from the web 16.

As the web 16 is passed intermittently through the die assembly 20, a plurality of web pieces 18 are die cut and punched out from the web 16 and are forced by punches 25 downwardly onto parallel rails 33 and onto a plurality of vertical pins 31. The pins extend upwardly through the rails 23 and are attached to a shuttle conveyor 30 located below rails 23. Next, the web remaining portion 16a from which pieces 18 have been removed is passed onward over roller 29 to a web scrap disposal or reclaiming step (not shown).

Figure 3:
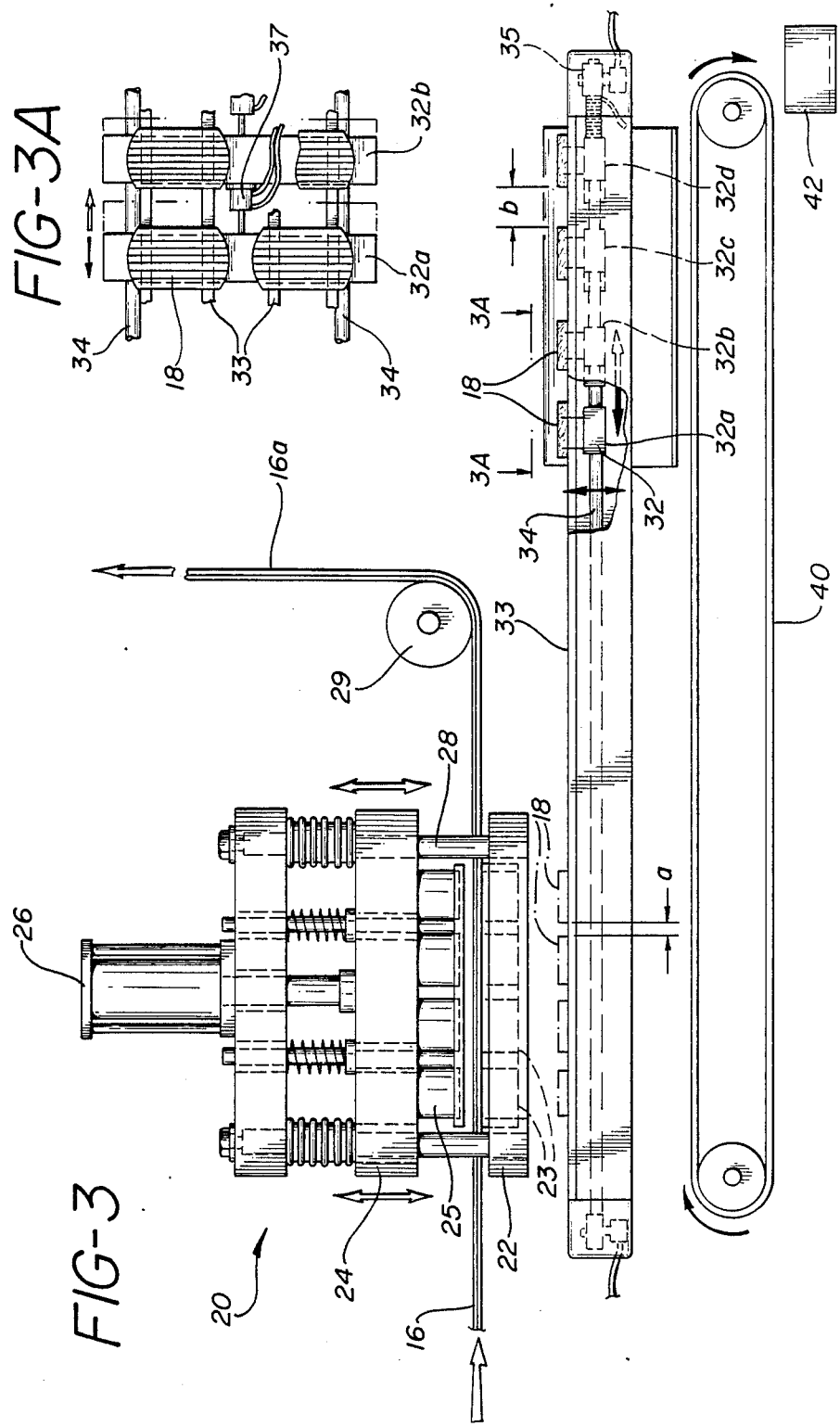
FIG. 3 shows an elevation view of a fibrous web sheet being passed through a matched cutting die assembly, including upper plug and lower body units located above a shuttle conveyor for moving apart the punched out web pieces.

The present invention is further described with reference to the FIG. 3 schematic view showing the die cutting and shuttle conveyor method steps and apparatus in more detail. As shown, the punched web pieces 18 from the cutting die assembly 20 are forced by punches 25 down onto multiple parallel rails 33 of the shuttle conveyor unit 30. It is pointed out that to utilize the web material 16 most efficiently, the die openings 23 in lower die unit 22 and mating punch members 25 are closely spaced in the horizontal plane, so that the resulting web pieces 18 of web 16 are closely spaced as shown by FIG. 2. However, because it is desired subsequently to have the web pieces 18 spaced further apart, shuttle conveyor device 30 is provided below the lower die body 22. The conveyor device 30 includes a horizontally movable shuttle 32 having pins 31 extending upwardly through parallel rails 33, and the punched out web pieces 18 are impaled onto pins 31 as they are forced by punch 25 from the die openings 23 onto the pins 31 and rails 33. Pieces 18 are impaled by the vertically oriented pins 31 attached to the shuttle 32. The shuttle 32 is then moved horizontally to the right on dual horizontal support rods 34 by a pneumatic device 35 located at one end of the conveyor. As shuttle 32 is moved carrying pieces 18, its segments 32a, 32b, 32c and 32d are moved apart from one another by pneumatic actuator devices 37 provided between the segments and are moved from an initial spacing dimension "a" between the pieces to a final spacing "b". The locations of the pressure actuator devices 37 relative to the shuttle segments 32 is shown more clearly by FIG. 3A. The shuttle unit 32 is then moved downwardly leaving the more widely spaced pieces 18 supported on the rails 33, and the shuttle is then returned to its original position to carry forward new pieces 18. From this separated position, the web pieces 18 can·be more conveniently picked up and moved to a further processing step (not shown). Any powder which may fall out of the web pieces 18 falls onto conveyor belt 40 and is deposited in a receptacle 42 for disposal or reuse.

Figure 4:
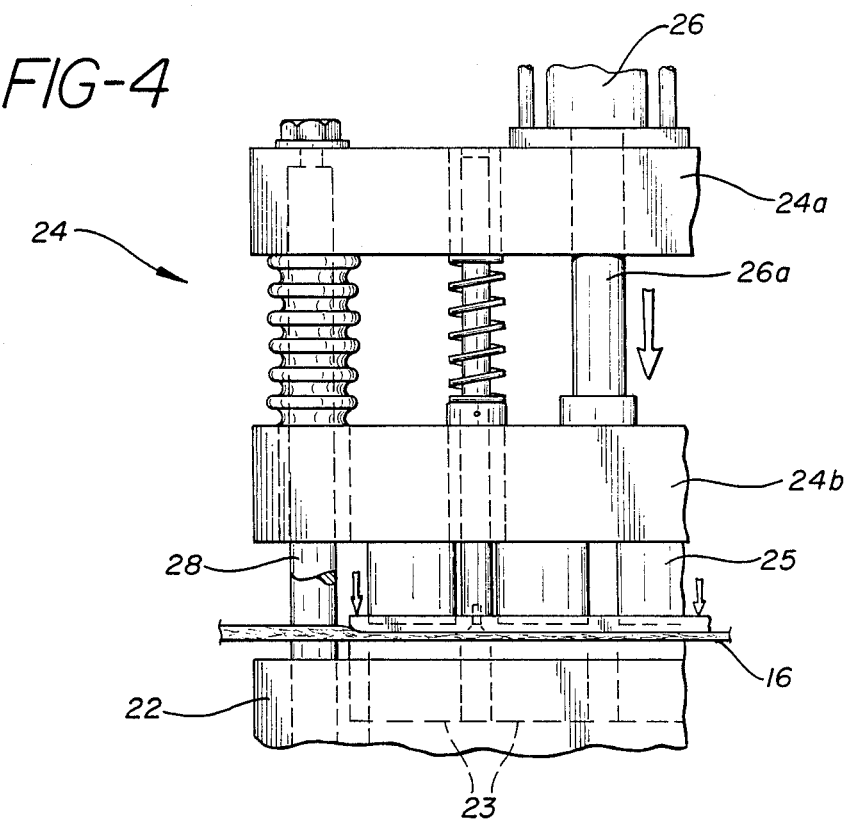
FIG. 4 shows a partial elevation view of the cutting die assembly of FIG. 3, with the punch shown when first contacting the web.
Figure 5:
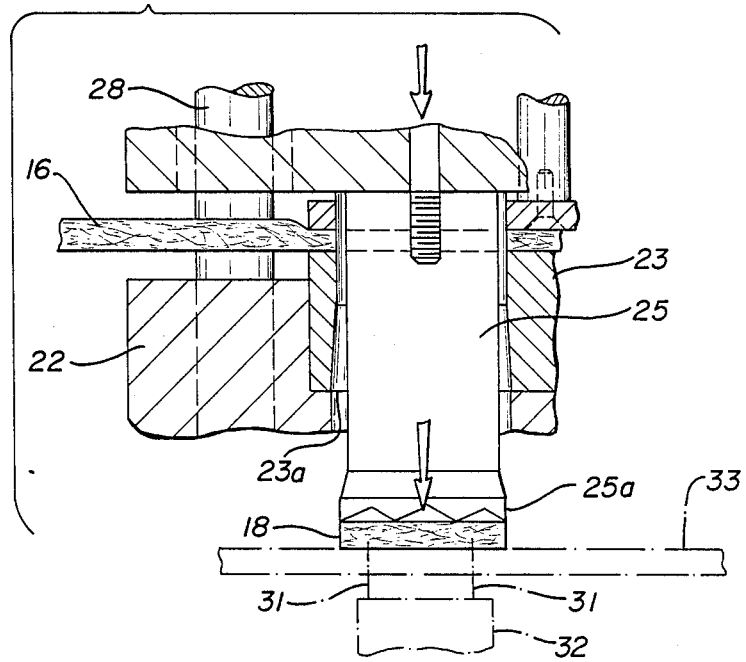
FIG. 5 shows a partial elevation view of the cutting die assembly of FIG. 3 after the punch has cut a web piece from the web and forced it downward onto the conveyor.

The construction and operation of the cutting die assembly 20 is described in greater detail with reference to FIGS. 4 and 5. The upper die unit 24 includes an upper plate 24a and lower plate 24b which is vertically movable relative to upper plate 24a and is accurately guided by the four vertical guide rods 28. In operation, lower plate 24b is moved downwardly by action of the hydraulic actuator cylinder 26 attached to piston rod 26a, and initially clamps web 16 against the lower die member 22. Then punches 25 descend further and cut through web 10 and enter openings 23 of lower die member 22. As best seen in FIG. 5, the punches 25 each have a beveled and serrated cutting edge 25a which facilitates cutting through the web 16. The cutting edge 25a is preferably serrated so that separated points or portions of the cutting edge contact the web first, after which the remaining portions of the cutting edge shear through the web until the pieces 18 are completely severed. The die cutting openings 23 are slightly tapered so as to provide a suitable relief clearance with punch 25 of 0.020-0.030 inches at the lower end 23a of the die opening.

The fibrous web may preferably consist of two layers of fibrous web material which are lightly bonded together and are compressed or embossed together along their edges as shown in FIG. 1. The web fiber diameter is usually less than about 0.002 inch and may be 0.0002-0.001 inch. The web can have a thickness of about 0.10 to 2.0 inches and preferably 0.5-1.0 inches. The web preferably contains an absorbent powder or particles incorporated among the fibers in such manner that any loss of the powder due to dusting out during cutting is minimal.

This invention will be further described by reference to the following example, which should not be construed as limiting in scope.

EXAMPLE

A continuous fibrous web is composed of two superimposed corrugated layers of fibrous material and has a flat embossed portion extending along each side and in a middle portion of the web. The corrugated web contains an absorbent powder provided into spaces between the corrugations. The web is passed to a cutting die assembly including a lower body unit containing eight openings each having the shape of the web pieces and an upper body unit containing eight punches each closely interfitting into the openings of the lower die unit with total lateral clearance 0.0004-0.0006 inch. The web is fed intermittently to the die assembly which cuts out eight individual web pieces and forces them downwardly onto upwardly extending pins of a shuttle conveyor. The resulting web pieces have characteristics as listed in Table 1 below.

TABLE 1

| Characteristics of Corrugated Fibrous Web Pieces | |
|---|---|
| Web material | polyester fibers |
| Web thickness, inches | 0.50-1.0 |
| Web width, inches | 18-20 |
| Number of corrugations, per inch | 3.5-4 |
| Absorbent powder contained in web, weight % of web | 100-150 |
| Powder particle size range | 100-400 microns |
| Number of cut out web pieces | 8 |

The eight web pieces are arranged in two rows of four pieces each on the shuttle conveyor. The adjacent pieces in each row are moved apart from each other by 1 inch by movement of the segments of the shuttle conveyor, each segment containing two upwardly extending pins which intersect and move the web pieces apart from each other.

From the above description it will be understood that numerous modifications and variations may be made to the present invention without departing from the broad scope of the invention, which is defined by the following claims.

We claim:

1. An apparatus for die cutting multiple pieces of fibrous material for incontinent pads or the like, the apparatus comprising:
    (a) means for feeding forward a continuous fibrous web to a cutting and transfer station;
    (b) a cutting die assembly at said cutting and transfer station, said cutting die assembly including a lower body unit having a plurality of shaped openings therein and a vertically movable upper body unit having a plurality of punch members each adapted to closely interfit into one of said die body openings with total clearance less than about 0.001 inch, so as to punch out a plurality of individual web pieces from the continuous web and thereby form a scrap material web;
    (c) shuttle conveyor means located below said die assembly and adapted to receive the punched out web pieces, said shuttle conveyor being adapted to move the web pieces forward to a further processing station; means associated with said shuttle conveyor means for increasing the spacing between adjacent punched out web pieces as they are moved to said further processing station by said shuttle conveyor means; and
    (d) means for withdrawing the scrap material web.

2. The apparatus according to claim 1, wherein the radial clearance between the die body opening and the mating punch is 0.0002-0.0008 inches.

3. The apparatus according to claim 1, wherein at least two parallel die openings are provided in said die assembly.

4. The apparatus according to claim 1, wherein the upper die unit includes a clamping member for stabilizing the web onto the die assembly lower unit and an inner punch member for shearing the web pieces from the continuous web.

5. A method of making multiple fibrous absorbent material pieces for use in an incontinent pad or the like comprising:
    providing a continuous fibrous web comprised at least in part of fibers having a fiber diameter of less than about 0.001 inch, said web having a thickness of 0.1-2.0 inch;
    intermittently advancing the web into a matched cutting die assembly containing a plurality of relatively closely spaced punch and die members having total clearance of less than about 0.001 inch between mating parts;
    intermittently operating the cutting die assembly to produce a plurality of fibrous absorbent material pieces;
    punching out said pieces from the web;
    depositing said punched out pieces onto conveyor means below said cutting die assembly;
    intermittently operating said conveyor means to carry said pieces away from said cutting die assembly for further processing;
    and increasing the spacing between adjacent punched out pieces on said conveyor means as the pieces are carried away for further processing.

6. The method according to claim 5 wherein said punched out pieces are impaled on pins projecting from the conveyor means and positively held thereby while moving away from under the cutting die assembly.

7. The method according to claim 6 wherein said pins are retracted from the punched out pieces when the pieces are carried to a station for further processing.

8. The method according to claim 7 wherein said conveyor means operates as a shuttle carrier and returns to receive a next batch of punched out pieces after said pins are retracted at the station for further processing.

9. The method according to claim 5 wherein said web is corrugated and contains a powder material, and collecting any powder dislodged from the web onto a moving belt located below the cutting die assembly.

* * * * *